(12) United States Patent
Boctor et al.

(10) Patent No.: US 7,867,167 B2
(45) Date of Patent: Jan. 11, 2011

(54) ULTRASOUND CALIBRATION AND REAL-TIME QUALITY ASSURANCE BASED ON CLOSED FORM FORMULATION

(75) Inventors: Emad M. Boctor, Baltimore, MD (US); Gregory D. Hager, Baltimore, MD (US); Gabor Fichtinger, Kingston (CA); Anand Viswanathan, Staten Island, NY (US)

(73) Assignee: Johns Hopkins University, Baltimore, MD (US)

( * ) Notice: Subject to any disclaimer, the term of this patent is extended or adjusted under 35 U.S.C. 154(b) by 665 days.

(21) Appl. No.: 11/578,071

(22) PCT Filed: Apr. 15, 2005

(86) PCT No.: PCT/US2005/013026

§ 371 (c)(1), (2), (4) Date: Jan. 17, 2008

(87) PCT Pub. No.: WO2005/099581

PCT Pub. Date: Oct. 27, 2005

(65) Prior Publication Data

US 2008/0269604 A1  Oct. 30, 2008

Related U.S. Application Data

(60) Provisional application No. 60/562,460, filed on Apr. 15, 2004.

(51) Int. Cl.
*A61B 8/00* (2006.01)
*G01B 7/00* (2006.01)

(52) U.S. Cl. .................................... 600/437; 73/1.75
(58) Field of Classification Search .............. 600/443, 600/451, 437; 73/1.86, 1.75
See application file for complete search history.

(56) References Cited

U.S. PATENT DOCUMENTS

| | | | | |
|---|---|---|---|---|
| 5,810,008 | A * | 9/1998 | Dekel et al. | 600/443 |
| 6,338,716 | B1 * | 1/2002 | Hossack et al. | 600/459 |
| 6,390,982 | B1 * | 5/2002 | Bova et al. | 600/443 |
| 6,604,404 | B2 * | 8/2003 | Paltieli et al. | 73/1.82 |
| 6,724,930 | B1 * | 4/2004 | Kosaka et al. | 382/154 |
| 7,090,639 | B2 * | 8/2006 | Govari | 600/437 |
| 2002/0183615 | A1 * | 12/2002 | Bucholz | 600/427 |
| 2004/0218792 | A1 * | 11/2004 | Spoonhower et al. | 382/128 |
| 2005/0085718 | A1 | 4/2005 | Shahidi | |

* cited by examiner

*Primary Examiner*—Eric F Winakur
*Assistant Examiner*—Lawrence N Laryea
(74) *Attorney, Agent, or Firm*—Venable LLP; Henry J. Daley (57) ABSTRACT

Disclosed is a system and method for intra-operatively spatially calibrating an ultrasound probe. The method includes determining the relative changes in ultrasound images of a phantom, or high-contrast feature points within a target volume, for three different ultrasound positions. Spatially calibrating the ultrasound probe includes measuring the change in position and orientation of the probe and computing a calibration matrix based on the measured changes in probe position and orientation and the estimated changes in position and orientation of the phantom.

20 Claims, 10 Drawing Sheets

ULTRASOUND CALIBRATION AND REAL-TIME QUALITY ASSURANCE BASED ON CLOSED FORM FORMULATION

This application claims the benefit to International Patent Application No. PCT/US2005/013026, filed on Apr. 15, 2005 and U.S. Provisional Patent Application No. 60/562,460, filed on Apr. 15, 2004, both of which are hereby incorporated by reference for all purposes as if fully set forth herein.

The research and development effort associated with the subject matter of this patent application was supported by the National Science Foundation under grant no. ERC 9731478.

BACKGROUND OF THE INVENTION

1. Field of the Invention

The present invention involves the field of ultrasound imagery. More particularly, the present invention involves spatial calibration of ultrasound probes for intra-operative use.

2. Discussion of the Related Art

Computer Integrated Surgery has revolutionized surgical procedures, whereby 3D imagery of a target volume is created to enable a surgeon to more precisely and accurately position surgical tools within a patient. To serve this purpose, the imaging system, or guidance modality, should provide 3D imagery in real time; it must not be excessively obstructive or burdensome in an operating environment; and it must provide 3D imagery with sufficient accuracy and precision to provide effective surgical planning and execution.

Ultrasound has become a popular guidance modality for medical procedures, due to its real-time operation, safety, low cost, and convenience of use in an operating room environment. Although it is not a "true 3D" imaging modality, such as Magnetic Resonance Imaging (MRI) and Computer Tomography (CT), techniques have been developed to convert multiple ultrasound 2D images into a 3D image in order to provide image guidance for surgeons while exploiting the benefits and conveniences of ultrasound.

Figure 1:
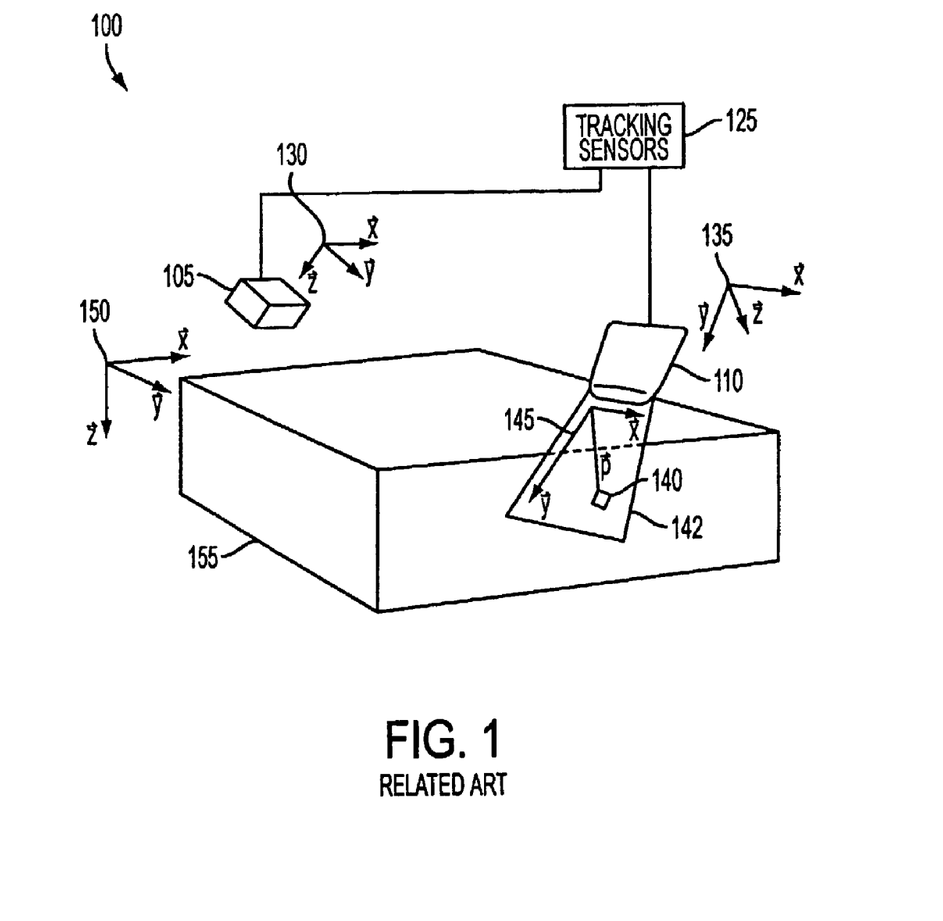
FIG. 1 illustrates components of an ultrasound imaging system according to the related art.

Components of a conventional ultrasound system 100 are illustrated in FIG. 1. The ultrasound system 100 includes a transmitter 105 having a transmitter reference frame 130; and an ultrasound probe 110 having a probe reference frame 135. The ultrasound probe 110 transmits and receives energy in a scan plane 142, and projects a plurality of pixels 140 in a pixel reference frame 145. A conventional ultrasound system 100 may also include tracking sensors 125 to monitor the position and orientation of the ultrasound probe 110. The ultrasound system 100 is used to collect multiple 2D ultrasound images, which are assembled into a 3D image space 155 having a construction reference frame 150 (hereinafter "construction frame").

In order to provide image guidance during a surgical procedure, 2D ultrasound images acquired by the ultrasound system 100 must be registered or mapped in real-time into a 3D image space 155, which encompasses a target volume within the patient undergoing surgery. Although there are ultrasound probes that acquire 3D images, these probes need to be spatially calibrated as well. Registering pixels from pixel reference frame 145 to the 3D image space 155 requires a transformation matrix encompassing a series of constituent coordinate transformation matrices: e.g., from the pixel frame 145 to the ultrasound probe reference frame 135; from the ultrasound probe frame 135 to the transmitter reference frame 130; and from the transmitter reference frame 130 to the construction frame 150. Of these transformation matrices, the most difficult to determine is the transformation matrix from the pixel reference frame 145 to the ultrasound probe reference frame 135 (hereinafter the "probe calibration matrix").

According to the related art, spatial calibration is the act of determining each of the aforementioned transformation matrices, which is typically done before a medical procedure. In related art spatial calibration, the ultrasound probe 110 is placed and oriented such that it acquires an image of a calibration target, or phantom, which has well defined spatial features. Using image processing techniques such as segmentation, the well defined features of the phantom are identified and located in the acquired ultrasound image, and the position and orientation of the phantom is derived from the segmented image. In the related art approach, images are acquired with the ultrasound probe 110 placed in a single position and orientation. If the position and location of the phantom are known relative to the construction frame 155, the probe calibration matrix can be derived. By comparing the locations of the identified imaged features of the phantom with known locations and relative orientations of these features, the orientation of the phantom may be determined relative to the orientation of the ultrasound probe, and the probe calibration matrix may be derived by correlating the segmented images of the phantom with the phantom's known spatial characteristics.

Image processing techniques such as segmentation are computationally intensive and may not be feasible to compute in real time, based on the number of images acquired. Typical segmentation is performed on several hundred images. The large number of images not only requires time to process, but it increases the likelihood of errors that may render the probe calibration matrix invalid.

According to the related art, once the transformation matrices, including the probe calibration matrix, are known, a pixel 140 may be registered into the 3D image space 155 defines by the construction frame 150. The transformation of a pixel 140 location from the pixel reference frame 145 to the construction frame 155 can be expressed as:

$$C_x = {}^C T_T \, {}^T T_R \, {}^R T_P P_x,$$

where $P_x$ is the location of pixel 140 in pixel reference frame 145; $C_x$ is the location of pixel 140 in construction frame 155; ${}^R T_P$ is the coordinate transformation matrix from the pixel reference frame 145 to the ultrasound probe reference frame 135 (i.e., the probe calibration matrix); ${}^T T_R$ is the coordinate transformation from the ultrasound probe reference frame 135 to the transmitter reference frame 130, which may be measured using tracking sensors 125; and ${}^C T_T$ is the coordinate transformation from the transmitter reference frame 130 to the construction frame 155, which may be measured.

The accuracy and precision of registering ultrasound image pixels 140 into the construction frame 155 is limited by the accuracy and precision of each of the above transformation matrices. The weakest link in this chain is the accuracy and precision of the probe calibration matrix ${}^R T_P$. Accordingly, a primary challenge in spatial calibration is in determining the probe calibration matrix ${}^R T_P$.

There are errors intrinsic to the conventional spatial calibration process that limit its precision and accuracy, including the following: imprecision in fabrication of the phantom, subsequent mechanical distortions of the phantom, lack of precision in characterizing the features of the phantom, spatial co-registration or ambiguities, and limits to numerical solution optimizations. As such, the quality of the calibration is limited to the accuracy and precision to which the phantom is characterized.

An additional disadvantage of the related art spatial calibration is that since it cannot be performed intra-operatively, partly because it cannot be performed in real time, it is vulnerable to subsequent changes that may render any or all of the calibration matrices invalid without warning. Such post-calibration changes may be brought on by mechanical alteration to the tracking sensors and changes in tissue temperature. The effect of post-calibration changes may include inaccurate 3D image, resulting in incorrect surgical instrument placement.

Although the above discussion involves ultrasound, the same issues may be encountered for any imaging system for which 2D images are assembled into a 3D image space. Or more generally, the same issues may arise in which a 2D imaging system is spatially calibrated in order to register image products into another reference frame.

SUMMARY OF THE INVENTION

Accordingly, the present invention is directed to ultrasound calibration and real-time quality assurance based on closed form formulation that substantially obviates one or more of the problems due to limitations and disadvantages of the related art. In general, the present invention achieves this by deriving a probe calibration matrix $^RT_P$ based on relative images of a phantom acquired from at least three positions and orientations, as opposed to deriving a probe calibration matrix $^RT_P$ from images of the phantom, from one position and orientation, that is correlated with known characteristics of the phantom.

An advantage of the present invention is to provide more reliable real-time ultrasound-based 3D imagery for use during medical procedures in that the ultrasound probe may be spatially calibrated intra-operatively. This helps mitigate post-calibration changes that may degrade the accuracy of 3D imagery without warning.

Another advantage of the present invention is to provide a more efficient and robust spatial calibration of an ultrasound probe. By spatially calibrating the ultrasound probe based on the relative differences between two or more images of the same phantom, the resulting calibration is less dependent on the precision to which the spatial characteristics of the phantom are known.

Another advantage of the present invention is to simplify the ultrasound probe calibration process. The present invention identifies pixels corresponding to prominent feature points on a phantom, as opposed to segmenting an image in order to reconstruct an image of the phantom, which is more computationally intensive.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, a method for spatially calibrating an ultrasound probe comprises placing the ultrasound probe in a first position and orientation relative to a phantom; measuring the first position and orientation of the ultrasound probe; acquiring a first ultrasound image of the phantom; determining a first transformation matrix corresponding to a phantom reference frame and a pixel reference frame, based on the first ultrasound image; repositioning the ultrasound probe in a second position and orientation relative to the phantom; measuring the second position and orientation of the ultrasound probe; acquiring a second ultrasound image of the phantom; determining a second transformation matrix corresponding to the phantom reference frame and the pixel reference frame, based on the second ultrasound image; and computing a probe calibration matrix based on the first position and orientation of the ultrasound probe, the first transformation matrix, the second position and orientation of the ultrasound probe, and the second transformation matrix.

In another aspect of the present invention, a system for performing intra-operative calibration of an ultrasound probe comprises a position and angle encoder for measuring a position and angle of the ultrasound probe; and a data system having a computer readable medium encoded with a program for computing a probe calibration matrix according to a closed form formulation, and according to relative changes between the locations of prominent feature points in a first and a second ultrasound image, wherein the first ultrasound image corresponds to a first ultrasound probe position, and the second ultrasound image corresponds to a second ultrasound probe position.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE ILLUSTRATED EMBODIMENTS

Figure 2:
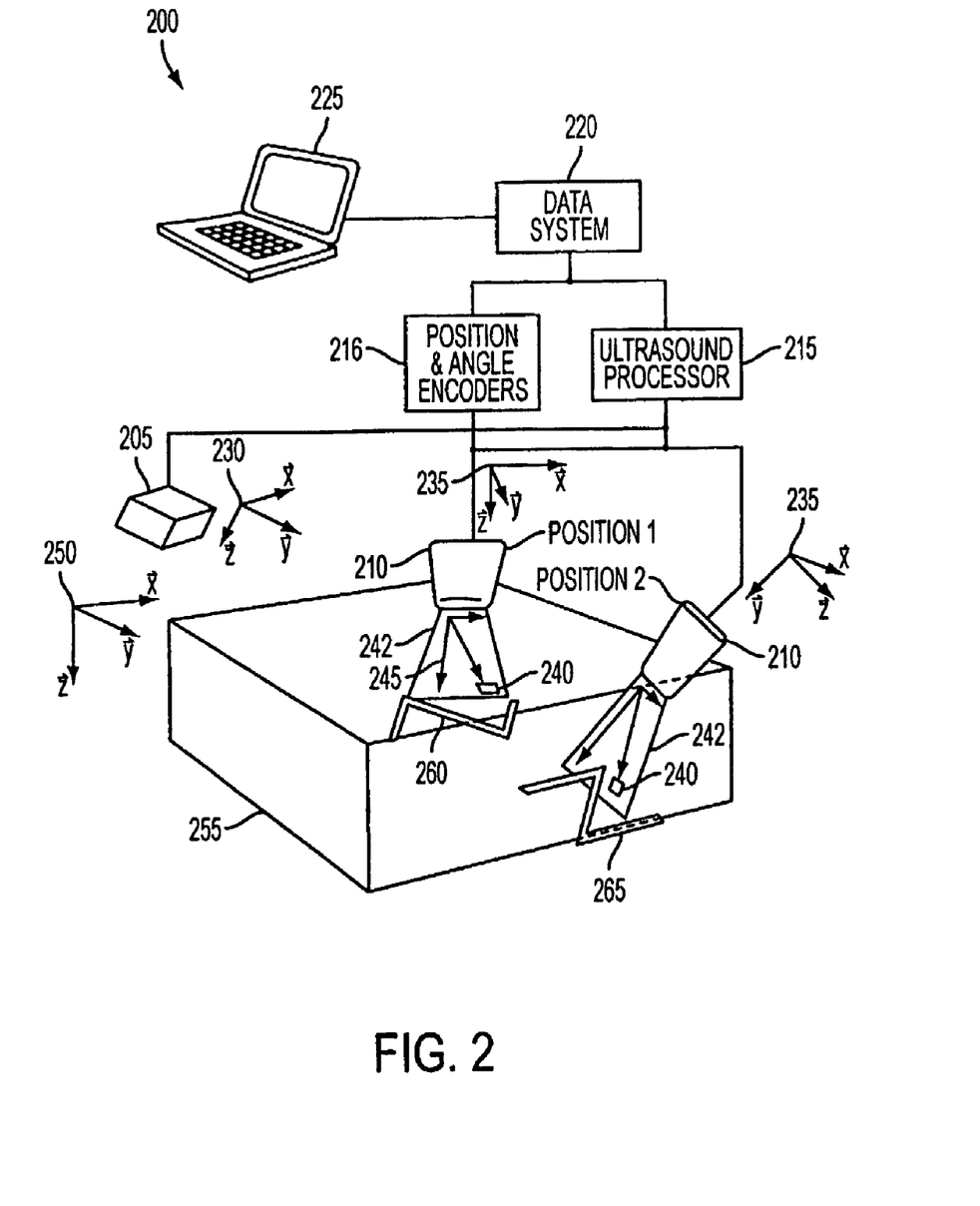
FIG. 2 illustrates an exemplary ultrasound imaging system according to the present invention.

FIG. 2 illustrates an exemplary ultrasound imaging system 200 according to the present invention. The imaging system 200 includes an ultrasound transmitter 205 having a transmitter reference frame 230; an ultrasound probe 210 having a probe reference frame 235; position and angle encoders 216 for measuring the position and orientation of the probe reference frame 235 relative to the transmitter reference frame 230; an ultrasound processor 215 for providing power and signals to, and receiving signals from, the ultrasound transmitter 205 and the ultrasound probe 210; a data system 220 for sending commands to and receiving data from the ultrasound processor 215 and the position and angle encoders 216; and a user interface 225 connected to the data system 220. The ultrasound probe 210 may transmit and receive energy in a scan plane 242, which includes a plurality of pixels 240 within the scan plane 242 and having a pixel reference frame 245.

The exemplary system 200 acquires ultrasound images, through use of the ultrasound probe 210, within a 3D image space 255 having a construction reference frame 250. Further, the exemplary system 200 may include one or more phantoms 260 and 265, which are located such that they can be imaged by the ultrasound probe 210, and wherein the phantoms 260 and 265 may be acoustically coupled to a target (not shown) to be imaged within the 3D image space 255. By acoustically coupling, it is understood that continuity in the propagation medium is maintained such that sound waves pass through.

FIG. 2 further illustrates a single ultrasound probe 210 in two separate positions, Position 1 and 2, in which the probe 210 may acquire images of the phantoms 260 and 265. Instead of two phantoms, there may be a single phantom, which may be imaged by the ultrasound probe 210 from multiple positions and orientations. For purposes herein, phantom 260 will be referred to in the case in which there is a single phantom. Although two positions are illustrated, at least three positions are generally required for computing the probe calibration matrix $^{R}T_{P}$ according to the present invention.

As used herein, the term "matrix," as in the probe calibration matrix $^{R}T_{P}$, may refer to any representation of a spatial relationship between coordinate frames, such as a quaternion.

For the purposes of illustration, this embodiment of the present invention may employ a SONOLINE™ Antares ultrasound scanner manufactured by Siemens Medical Solutions, USA, Inc., Ultrasound Division, Issaqua, Wash. with a Siemens VF 10-5 linear array probe held in a rigid attachment mounted on an adjustable arm. However, it will be readily apparent to one skilled in the art that other commercially available ultrasound scanners may be used.

In this exemplary embodiment of the present invention, the position and angle encoders 216 include multiple optical markers attached to the ultrasound probe 210, which are tracked using, for example, an OPTOTRAK™ device, manufactured by Northern Digital, Inc. It will be readily apparent to one skilled in the art that alternate devices and systems for providing real-time measurements of position and orientation of the ultrasound probe 210 may be used and are within the scope of the present invention.

The data system 220 may include one or more computers, which may be networked together either locally or over a network. The data system 220 includes software (hereinafter "the software") for implementing processes according to the present invention. The software may be stored and run on the data system 220, or may be stored and run in a distributed manner between the data system 220, the ultrasound processor 215, and the user interface 225.

Figure 3:
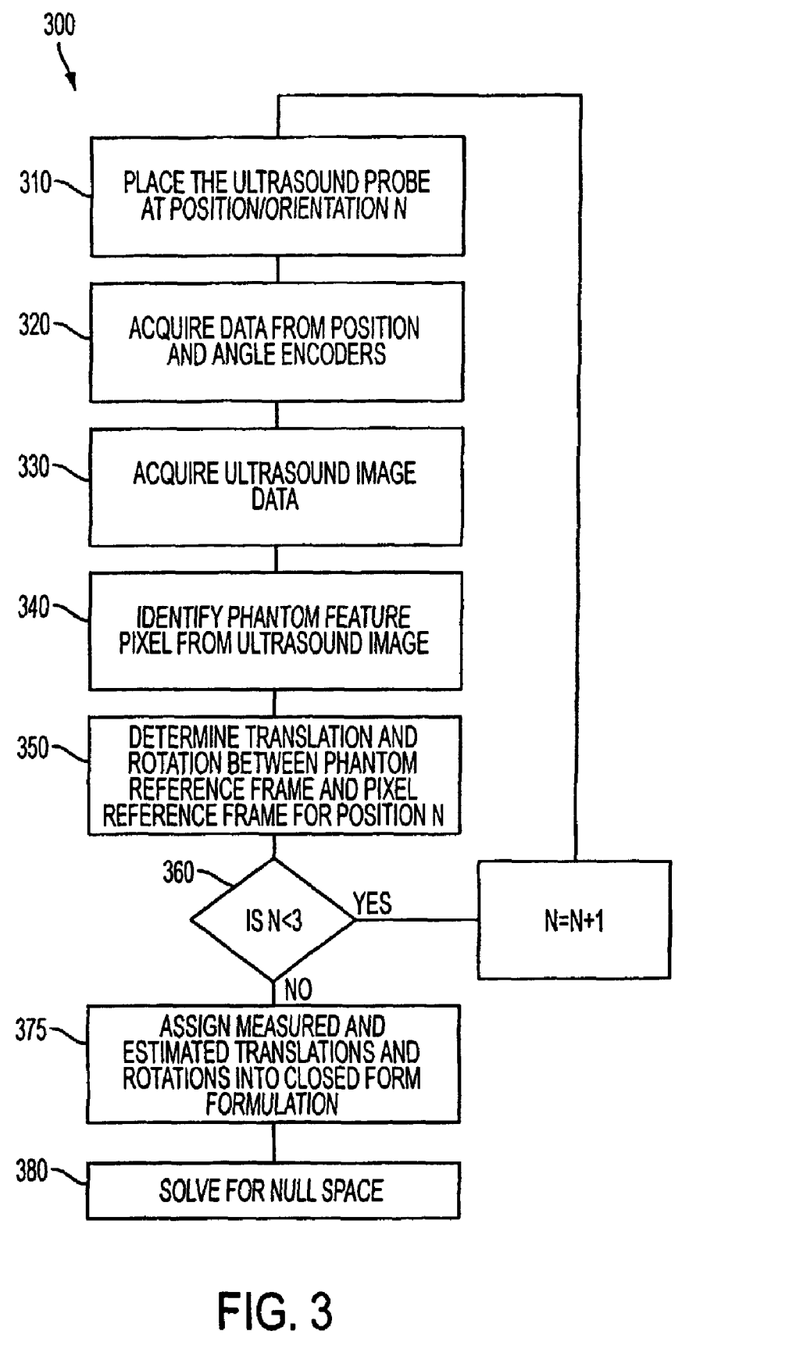
FIG. 3 illustrates an exemplary spatial calibration process according to the present invention.

FIG. 3 illustrates an exemplary process 300 for providing real-time spatial calibration according to the present invention, which may be implemented by the software. Process 300 may be used in conjunction with system 200, illustrated in FIG. 2, in which a single phantom 260 is used.

In step 310, the ultrasound probe 210 is placed in position 1 of N, wherein N may be at least three. Position 1 may be arbitrary or predetermined. Either way, the position should be such that the phantom 260 is within the scan plane 242 of ultrasound probe 240 wherein prominent feature points within the phantom 260 are readily identifiable in the acquired ultrasound image.

In step 320, the software acquires position and angle data of ultrasound probe 210 from the position and angle encoders 216 and stores the corresponding data values in memory. The software may acquire and store position and angle data of the ultrasound probe 210 exclusively while the ultrasound probe 210 is in position 1, or the software may continuously acquire and store position and angle data values throughout exemplary process 300. The software may provide time tag information corresponding to the position and angle data such that the time tag data may be used to synchronize the position and angle data with the ultrasound data acquired from the ultrasound processor 215.

In step 330, the ultrasound processor 215 acquires and processes ultrasound image data from the ultrasound probe 210 while the ultrasound probe is held in position 1. The software then receives ultrasound image data from the ultrasound processor 215 and stores the corresponding data values in memory. The software may acquire ultrasound data continuously throughout exemplary process 300, along with time tag data, and may store the ultrasound and time tag data values so that the ultrasound data may be synchronized with similarly time tagged position and angle data acquired from the position and angle encoders 216. If the data system 220 continuously acquires and stores ultrasound data values throughout exemplary process 300, the data system may additionally acquire and store data from the user interface 225, along with corresponding time tag data, which may provide a flag indicating that ultrasound data values corresponding to a given time were acquired while the ultrasound probe was in position 1.

Figure 4:
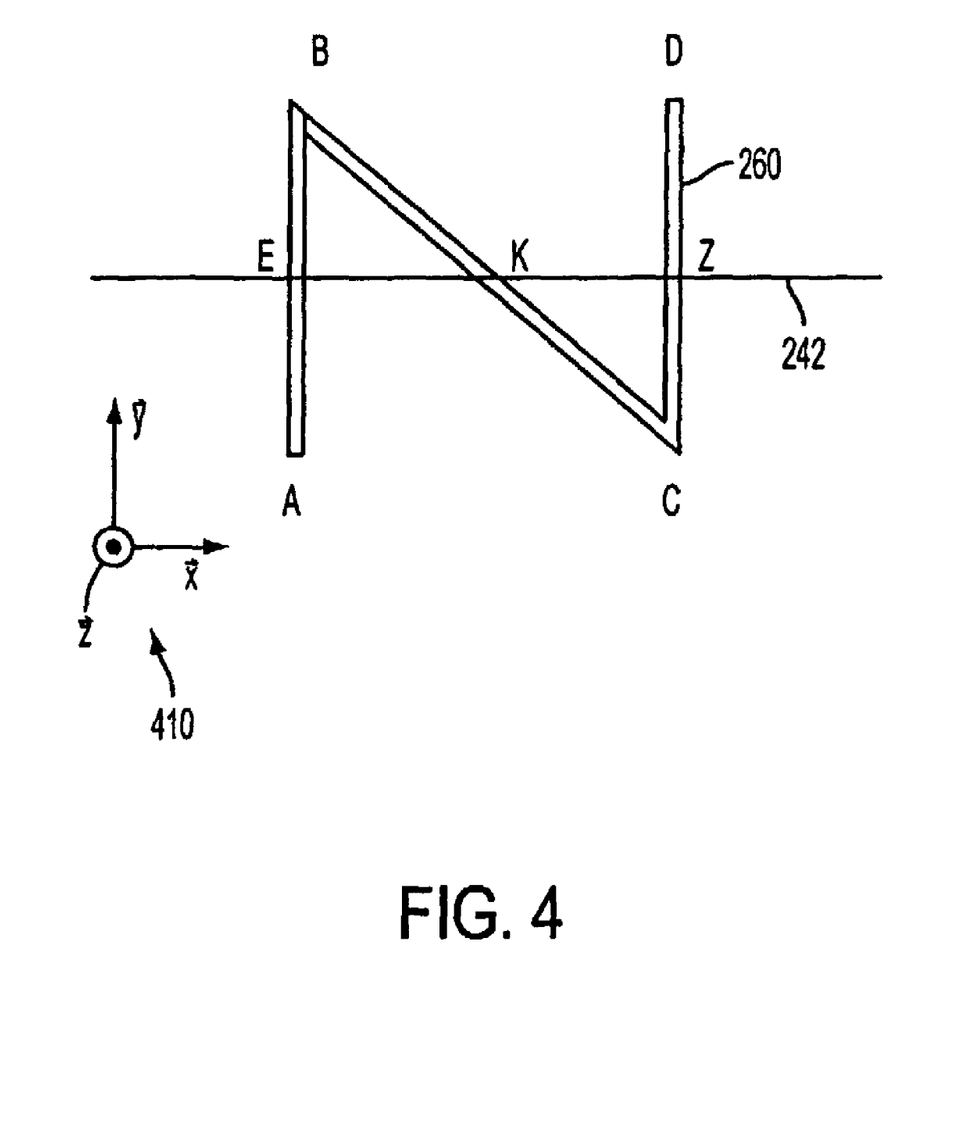
FIG. 4 illustrates an exemplary phantom according to the present invention.

In step 340, prominent feature points corresponding to the phantom 260 are identified from the ultrasound data acquired in step 330, as illustrated in FIG. 4. The prominent feature points may be selected by the user via the user interface 225 by, for example, selecting the point with a cursor and mouseclick. Alternatively, the software may automatically identify prominent feature points using image processing techniques that are known to the art.

FIG. 4 illustrates an exemplary phantom 260, along with its reference frame 410, and a scan plane 242 impinging on the phantom 260. In a particular embodiment, the phantom 260 may include a matrix of N-shaped wires stretched between two parallel plates. In order for the phantom 260 to be used intra-operatively, it should be acoustically coupled with a target volume, such as a patient undergoing surgery, such that the user may periodically position the ultrasound probe 210 in a given position 1 and position 2 during an operation. When being imaged by the ultrasound probe 210, the scan plane 242 may intersect a plane defined by the phantom at points E, K, and Z, as illustrated in FIG. 4. The x and y coordinate of the center point K of the phantom 260 in the phantom reference frame 410 may be determined from the relations:

$$x_k = x_b + (KE/EZ) \cdot (x_c - x_b), \text{ and } y_k = y_b + (KE/EZ) \cdot (y_c - y_b),$$

in which $x_k$ and $y_k$ are the coordinates of the center image point K of the phantom 260 in the phantom reference frame 410; $x_b$ and $y_b$ are the coordinates of point B on the phantom 260 in the phantom reference frame 410; and $x_c$ and $y_c$ are the coordinates of point C on the phantom 260 in the phantom reference frame 410.

In step 350, with the coordinates of the center point K determined, the software then computes a coordinate transformation between the ultrasound probe reference frame 245 and the phantom reference frame 410. The transformation may be accomplished by, for example, Horn's quaternion rigid registration method, as described in B. Horn, *Closed-form solution of absolute orientation using unit quaternions*, Journal of the Optical Society of America A, Vol. 4, page 629, April 1987, which is incorporated herein by reference. Other techniques may be used, such as those employed to transform a set of points between coordinate systems, as is done in the fields of photogrammetry. The result of this transformation is a translation and rotation of the image of the phantom 260 from the phantom reference frame 410 to the pixel reference frame 245.

In step 360, the software determines if there are more positions at which to acquire ultrasound data. If so, steps 310-350 are repeated for a new position. The next position may be chosen arbitrarily, or determined prior to executing the exemplary process 300. The next position should be chosen such that the phantom 260 is located within the scan plane 242 of the ultrasound probe 210, and that prominent feature points on the phantom 260 will be visible in the ultrasound imagery acquired by the ultrasound probe 210, as illustrated in FIG. 4. In a particular embodiment of the present invention, steps 310-350 are iterated 3 times.

In step 375, the software retrieves the stored data values for the following: the translation and rotation of the phantom 260 from the phantom reference frame 410 to the pixel reference frame 245 when the ultrasound probe 240 was in each position; and the position and angle of the ultrasound probe 240, as measured by the position and angle encoders 216, when the ultrasound probe was in each position In step 375, the software assembles this data into a closed form formulation for determining the probe calibration matrix $^R T_P$ according to the present invention and then derives the probe calibration matrix $^R T_P$ from the closed form formulation. The closed form formulation is based on the homogeneous matrix equation AX=XB, in which A is the relative coordinate transformations between the locations of the respective pixels corresponding to the prominent feature points of the phantom; B is the relative coordinate transformation between ultrasound prove reference frame at position 1 and position 2, as measured by the position and angle encoders; and X is the probe calibration matrix $^R T_P$. This homogeneous matrix equation may be expressed in software as the following:

$$\begin{bmatrix} I_9 - R_{a12} \otimes R_{b12} & 0_{9 \cdot 3} & 0_{9 \cdot 3} \\ I_3 \otimes t^t_{b12} & I_3 - R_{a12} & -D_{u12} \\ I_9 - R_{a23} \otimes R_{b23} & 0_{9 \cdot 3} & 0_{9 \cdot 3} \\ I_3 \otimes t^t_{b23} & I_3 - R_{a23} & -D_{u23} \end{bmatrix} \begin{pmatrix} vec(R_x) \\ t_x \\ \lambda \end{pmatrix} = \begin{pmatrix} 0_{9 \cdot 1} \\ 0_{3 \cdot 1} \\ 0_{9 \cdot 1} \\ 0_{3 \cdot 1} \end{pmatrix}$$

where I is an identity matrix; $R_{a12}$ and $R_{a23}$ are the rotations of the pixel reference frame 245 from position 1 to position 2, and from position 2 to position 3, respectively; $R_{b12}$ and $R_{232}$ are the respective rotations of the probe reference frame 235 from position 1 to position 2 and from position 2 to position 3, as measured by the position and angle encoders 216; $t_{b12}^t$ and $t_{b23}^t$ are respectively the transverse of the translation vectors corresponding to the translation of the probe reference frame 235 from position 1 to position 2 and from position 2 to position 3, as measured (for example, in mm) by the position and angle encoders 216; $D_{u12}$ and $D_{u12}$ are the translation vectors of the pixel reference frame 245 going from position 1 to position 2; $t_x$ is the translation vector component corresponding to the calibration matrix (to be solved); $R_x$ is the rotational component corresponding to the calibration matrix (to be solved); and λ is a vector of translational scale factors, wherein each scale factor converts the translation from number of pixels to a distance, such as millimeters. Of these variables, $R_a$ and $D_u$ are obtained by estimating the translation and rotation of the prominent feature points of the phantom 260 between position 1 and 2; and $R_x$, $t_x$, and λ are the values to be solved using the above formulation. The ⊗ symbol refers to the Kronecker product of two matrices; and the vec( ) operator creates a column vector from a matrix as follows:

$$vec(A) = \begin{bmatrix} a_{11} \\ a_{12} \\ \vdots \\ a_{1m} \\ a_{21} \\ a_{22} \\ \vdots \\ a_{nm} \end{bmatrix}$$

The rotation and translation corresponding to the probe calibration matrix $^R T_P$ may be derived by extracting a unique solution from the null space associated with the above formulation using the unity constraint to the first nine coefficients representing the rotation $R_x$. As is known in the art, extracting the null space involves solving the closed form solution and selecting the vector corresponding to the lowest coefficient.

If more than three positions are to be used, the left-most array in the closed form solution may be concatenated to include the $I_9-R_{a12} \otimes R_{b12}$ $0_{9 \cdot 3}$ $0_{9 \cdot 3}$ and $I_3 \otimes t_{b12}^t$ $I_3-R_{a12}-D_{u12}$ expressions for subsequent motions to additional positions. Generally, the more motions used, the more precise the probe calibration matrix $^R T_P$, at the expense of speed of computation.

An alternate approach is to solve the above formulation in two steps, wherein the rotation $R_x$ is extracted first, and then the translation $t_x$ and its associated scale factor λ are subsequently extracted. By solving for and extracting the scale factor vector λ, the calibration matrix may account for non-rigidity of the transformation between the pixel reference frame 245 and the probe reference frame 235, as opposed to a rigid transformation, in which case the scale factor λ may be a scalar. The rigid transformation case is described in the context of robotic hand-eye coordination by N. Andreff, R. Horaud, and B. Espiau, *Robotic Hand-Eye Calibration Using Structure-from-Motion*, The International Journal of Robotics Research, Vol. 20, No. 3, pp. 228-248, the contents of which are incorporated herein by reference.

With the rotation $R_x$, $t_x$ translation, and scale factor vector λ derived from the null space of the above formulation, the probe calibration matrix $^R T_P$ may be assembled according to the following relation:

$$^R T_P = \begin{bmatrix} & & & t_x \\ & R_x & & t_y \\ & & & t_z \\ 0 & 0 & 0 & 1 \end{bmatrix} = \begin{bmatrix} & & & \lambda_x u_x \\ & R_x & & \lambda_y u_y \\ & & & \lambda_z u_z \\ 0 & 0 & 0 & 1 \end{bmatrix}$$

where (ux, uy, uz) is the translation vector in number of pixels, and the scale factor λ converts the number of pixels into distance, such as millimeters.

The software may then store the constituent values of the probe calibration matrix $^{R}T_P$ for use in subsequent pixel registration from the pixel reference frame 245 into the 3D image space 255 defined by the reference frame.

Figure 5:
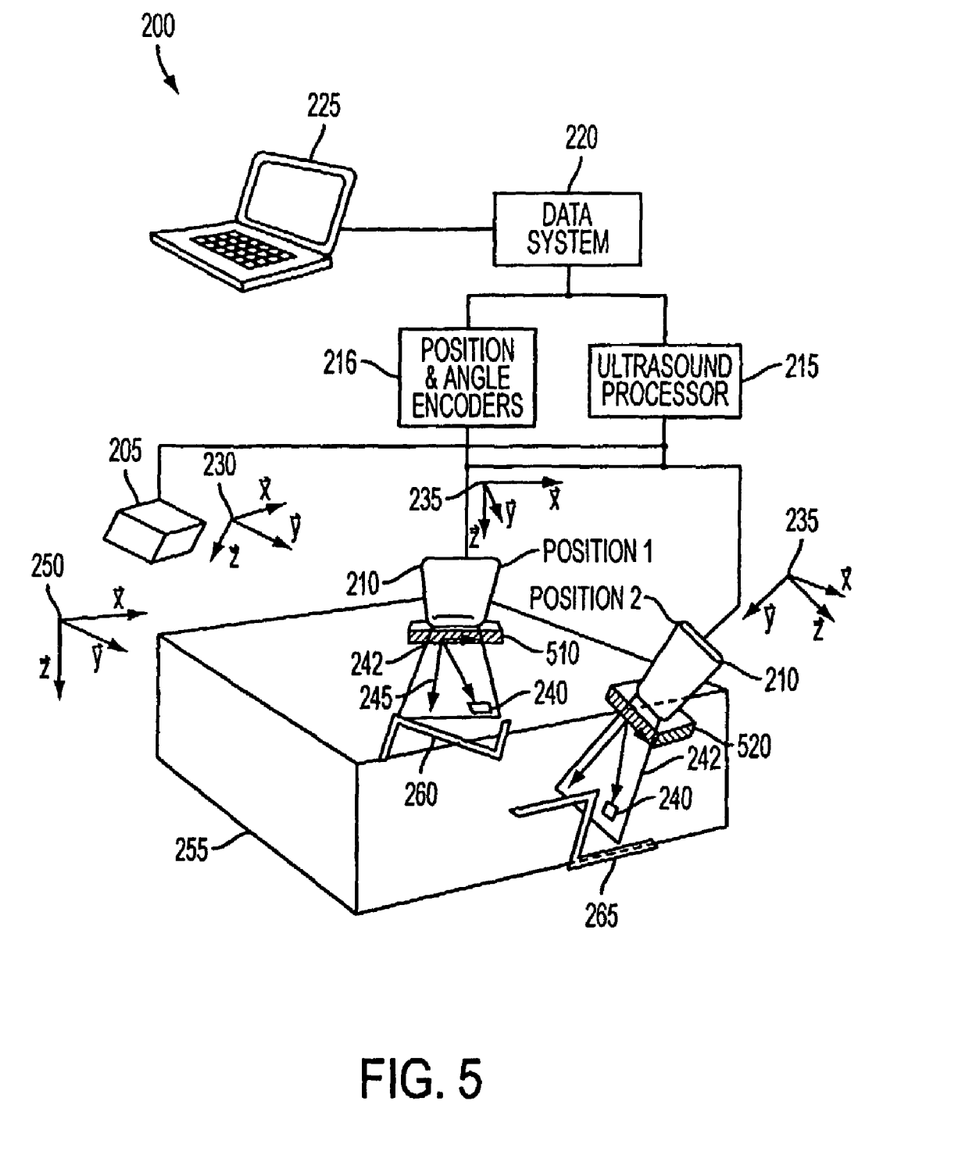
FIG. 5 illustrates an exemplary ultrasound imaging system, which includes at least one docking station.

FIG. 5 illustrates still another embodiment of the present invention, where exemplary system 200 includes one or more docking stations 510 and 520. The docking stations 510 and 520 are each in a substantially fixed position and orientation relative to the phantom 260, and each includes an acoustically coupled fixture for placing the ultrasound probe 210 in a precise position and angle relative to the construction frame 255. For example, by having two docking stations 510 and 520, one at position 1 and another at position 2, the user may place the ultrasound probe 210 more precisely at each of the two positions, which may improve the precision and accuracy of the measured position and orientation of the probe reference frame 245.

Multiple ultrasound images may be acquired per position, with each image being used to compute a separate probe calibration matrix. For example, if 3 positions are used, and 10 images are acquired per position, then it is possible to compute 10×9×8=720 probe calibration matrices. Similarly, if 6 images are taken per position, if 3 positions are used, then 6×5×4=120 probe calibration matrices may be generated. Computing the mean and standard deviation of any or all of these probe calibration matrices will provide an indication of the precision of the calibration.

Figure 6:
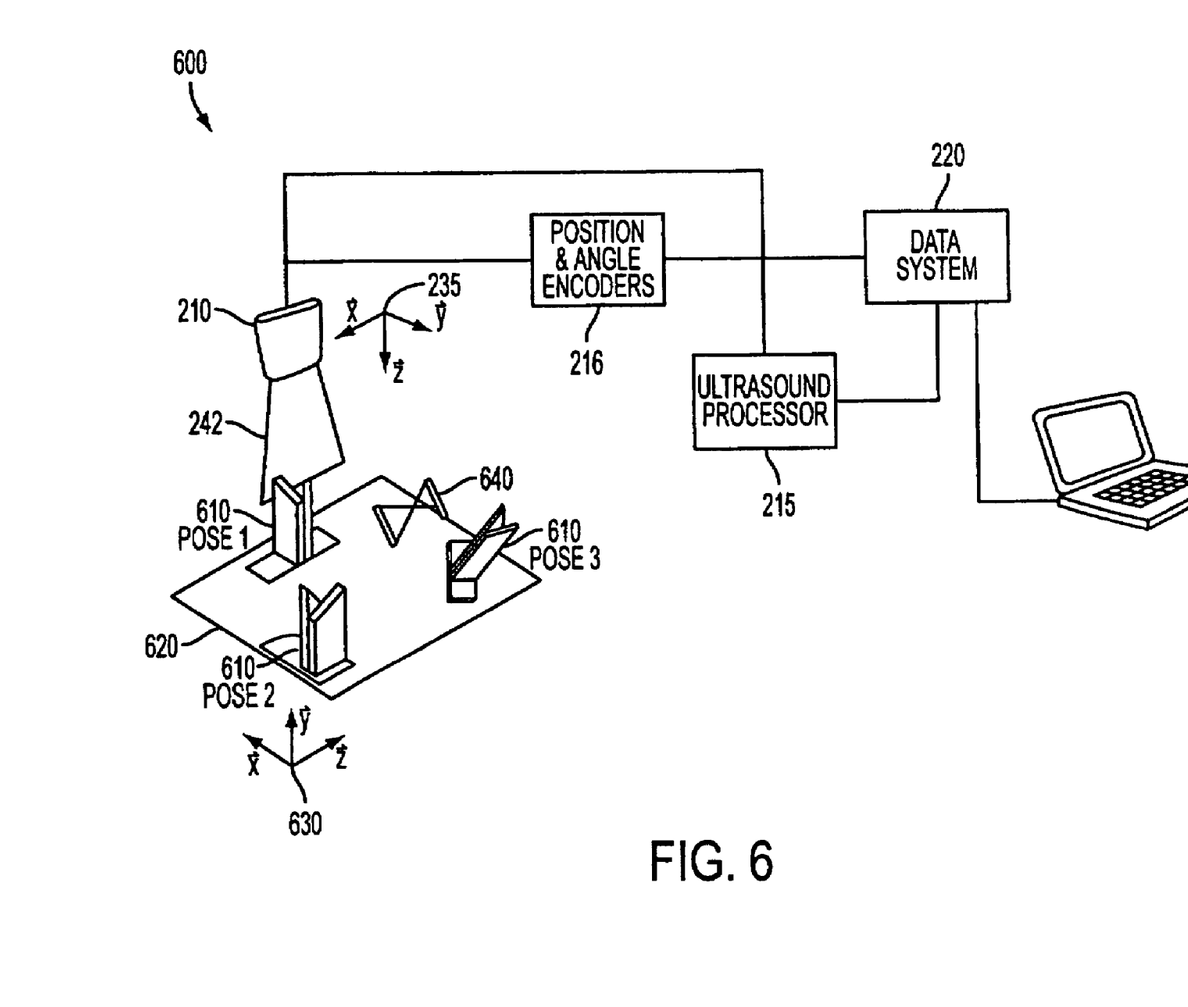
FIG. 6 illustrates an exemplary ultrasound imaging system that uses double-wedge phantoms.

FIG. 6 illustrates another embodiment of the present invention, in which imaging system 600 includes certain substantially similar components to exemplary system 200. However, system 600 also includes three double-wedge phantoms 610 mounted on a base plate 620, which has a base plate reference frame 630; and a cross-wire structure 640, which is located such that it may be imaged by the ultrasound probe 210 simultaneously with any of the double-wedge phantoms 610. The base plate 620 may have holes located and so that double-wedge phantoms 610 may be affixed to the base plate 620. The double-wedge phantoms 610 may be precisely located so that their relative locations are precisely known. In a particular embodiment, the double-wedge phantoms 610 are rigidly mounted so that their relative locations are known to within 100 μm. The double-wedge phantoms 610 and the base plate 620 may be immersed in an acoustically coupling material, such as a gel or water.

Exemplary system 600 may be used in conjunction with exemplary process 300. In using exemplary system 600, the ultrasound probe 210 is positioned and oriented to acquire images of the double wedge phantom 610 at pose 1 in step 310. As used herein, "pose" refers to the position and orientation of a given double-wedge phantom 610. Ultrasound images and probe position and angle data is then acquired in steps 320-350. Steps 310-350 may be iterated, whereby the position and orientation of the ultrasound probe 210 may be adjusted based on the translation and rotation determined in step 350.

In step 340, the images of the double-wedge phantom 610 are identified in an ultrasound image. FIGS. 7A-7D illustrate different scenarios in which an ultrasound beam 705 transmitted by the ultrasound probe 210 impinges on wedge features 710 and 720 of double-wedge phantom 610, and how the reflected energy from the transmitted beam 705 is distributed. FIGS. 8A-8D illustrate how the wedges 710 and 720 may appear in a resulting ultrasound image 732.

Given the shape of the double-wedge phantom 610, any translational offset or angular misalignment in the transmitted beam 705 relative to the pose of the double-wedge phantom 610 is manifested in the ultrasound image 732. By using the ultrasound image 732 as a form of feedback, the position and orientation of the probe 210 may be adjusted to correct it for any misalignment and translational offset.

Figure 7A:
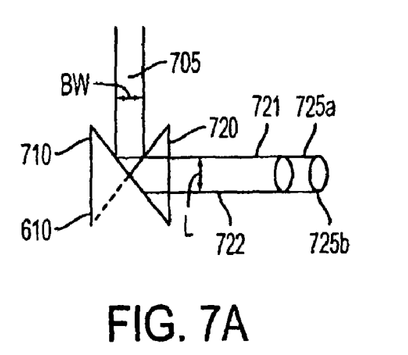
FIGS. 7A-7D illustrate the effects of misalignment and offset between an ultrasound probe and a double-wedge phantom, and their effects.
Figure 8A:
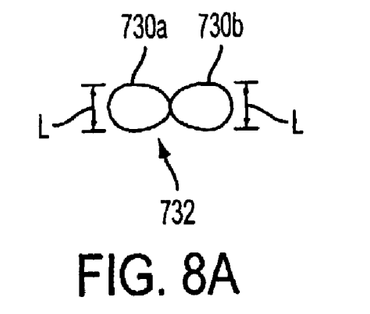
FIGS. 8A-D illustrate ultrasound images, and how misalignment and offset between an ultrasound probe and a double-wedge phantom are apparent in the images.

FIGS. 7A and 8A correspond to a scenario in which the transmitted beam 705 is aligned with the pose of the double-wedge phantom 610 with no translational offset. Line 721 refers to the "early echo," or the first reflected energy of the transmitted beam 705 to impinge on either wedge 710 and 720. Line 722 refers to the "late echo," or the end of the reflected energy from the transmitted beam 705. Elements 725a and 725b refer to the geometry of the reflected energy, in which the dimension L corresponds to the length of the reflected energy, which is a function of the beam width BW and the slope of the wedge 710 or 720.

FIG. 8A illustrates an exemplary ultrasound image 732 corresponding to FIG. 7A. In FIG. 8A, the acoustic energy reflected from wedge 710 results in a "cloud" image 730a; and the acoustic energy reflected from wedge 720 results in cloud 730b. Features 730a and 730b are referred to as clouds since the acoustic energy in transmitted beam 705 spatially and temporally spreads as a result of the divergence of the transmitted beam 705, the shape of the acoustic pulse transmitted by the ultrasound probe 210, and the angle of the wedge from which the energy is reflected. Since the transmitted beam 705 is aligned with the pose of the double-wedge phantom, clouds 730a and 730b have substantially the same height, which corresponds to dimension L, which is due to the fact that the transmitted beam 705 impinges on wedges 710 and 720 at substantially the same (and opposite) angle. Further, clouds 730a and 730b are located substantially "side by side" in ultrasound image 732, which is due to the fact that there is substantially no translational offset between the center of the transmitted beam 705 and the point at which wedges 710 and 720 cross.

The beam width BW of the transmitted beam may be computed from the height L of clouds 730a and 730b according to the relation BW=L·tan(30°). It will be readily apparent that angles other than 30° may be used, which may result in differing sensitivities to angular misalignment and translational offset.

Figure 7B:
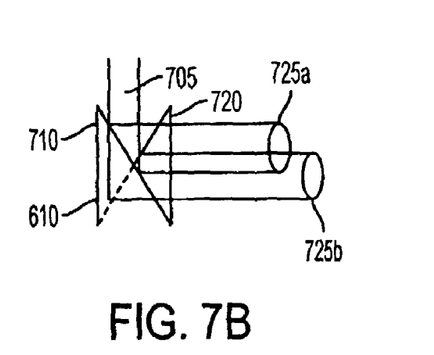
Figure 8B:
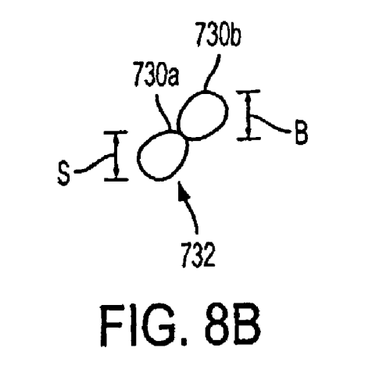

FIG. 7B illustrates how acoustic energy may be reflected from wedges 710 and 720 when the transmitted beam 705 is angularly aligned with the pose of the double-wedge phantom 610, but in which the transmitted beam 705 has a translational offset relative to wedges 710 and 720. In FIG. 8B, clouds 730a and 730b have substantially the same height, but are offset from one another in a manner proportional to the translational offset of the transmitted beam 705.

Figure 7C:
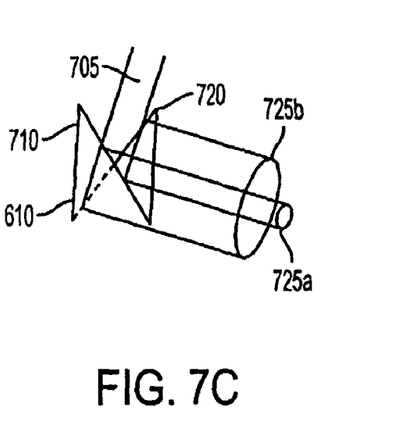
Figure 8C:
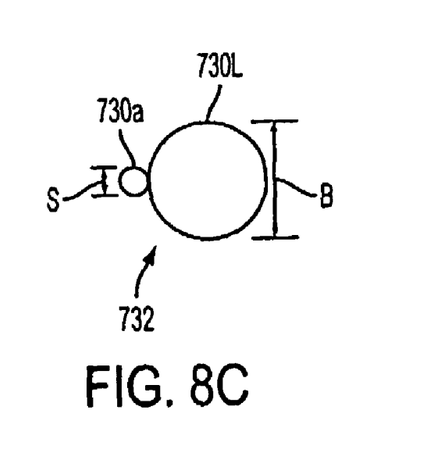

FIG. 7C illustrates how acoustic energy may be reflected from wedges 710 and 720 when the transmitted beam is angularly misaligned (at angle α) with the pose of the double-wedge phantom 610, but does not have any translational offset. As illustrated in FIG. 8C, clouds 730a and 730b have different heights S and B, wherein the height differential is proportional to the misalignment angle according to the following relation:

$$\frac{\tan(30° - \alpha)}{\tan(30° + \alpha)} = \frac{S}{B}$$

where 30° is the magnitude of the angle of wedges 710 and 720. As mentioned earlier, angles other than 30° may be used, which may result in different sensitivities to angular misalignment and translational offset.

Figure 7D:
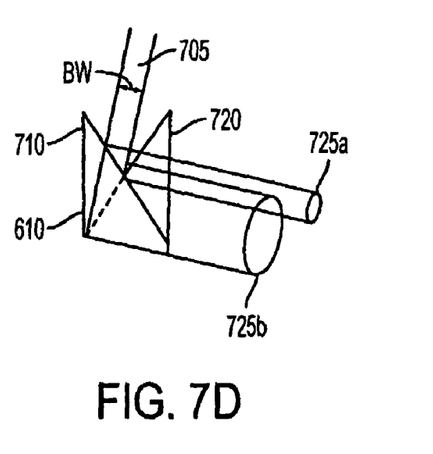
Figure 8D:
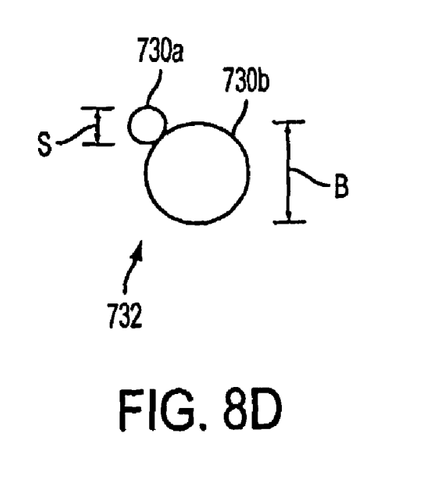

FIG. 7D illustrates how acoustic energy may be reflected from wedges 710 and 720 with a transmitted beam 705 impinging on the double-wedge phantom 610 with both an angular misalignment with the pose of the double-wedge phantom 610 and an translational offset. As illustrated in FIG. 8D, the resulting clouds 730a and 730b in the ultrasound image 732 have different heights S and B, the difference of which is proportional to the misalignment angle; and the clouds 730a and 730b are offset in a manner proportional to the translational offset of the transmitted beam 705.

In step 350, the heights of the clouds 730a and 730b, and their offset, may be determined automatically through image processing techniques known to the art. Alternatively, the heights of the clouds 730a and 730b and their offset may be determined by having the user place a cursor on the top and bottom of clouds 730a and 730b, and click a mouse. With the cloud size differential and cloud offset determined, the translation and rotation from the reference frame of the double-wedge phantom 610 to the pixel reference frame 245 may be determined.

According to this exemplary embodiment of the present invention, the user may adjust the position and orientation of the ultrasound probe 210 to substantially eliminate the angular misalignment and translational offset of the ultrasound probe 210 relative to the double-wedge phantom 610. The user may employ the ultrasound images of the wedges 710 and 720, like those illustrated in FIGS. 8A-8D, for feedback. If this is done, the translation and rotation between the reference frame of the double-wedge phantom 610 and the pixel reference frame 235 will be more precise.

In step 375, the software computes the closed form formulation as is done with exemplary system 200, except that the relative coordinate transformation A (from the aforementioned AX=XB homogeneous equation) may correspond to the following relation:

$$A = U_k W_{k,k+1} U_{k+1}^{-1}$$

where $U_k$ is the transformation matrix from the coordinate frame of the double-wedge phantom 610 at pose k to the pixel coordinate frame 245; $U_{k+1}^{-1}$ is the inverse of the transformation matrix from the coordinate frame of the double-wedge phantom 610 at pose k+1 to the pixel coordinate frame 245; and $W_{k,k+1}$ is the transformation matrix from the coordinate frame of the double-wedge phantom 610 at pose k to the double-wedge phantom 610 at pose k+1. Of these, $W_{k,k+1}$ is known, since it depends on the precision to which the base plate 620 was machined and characterized. With the closed form formulation assembled, the software extracts a unique solution from the null space in step 380.

Figure 9:
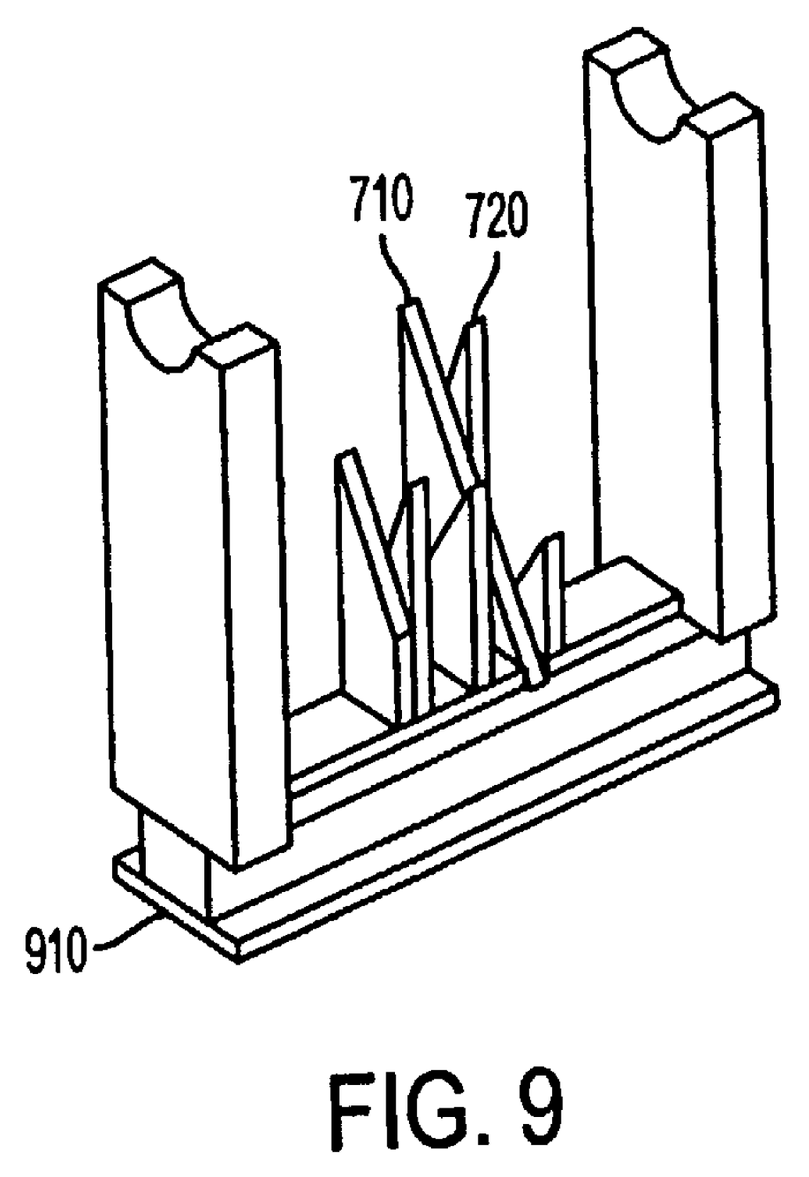
FIG. 9 illustrates an exemplary double-wedge phantom according to the present invention.

FIG. 9 illustrates an exemplary double-wedge phantom 910 according to the present invention. The double-wedge phantom 910 has multiple sets of wedges 710 and 720, each at different heights. Having multiple sets of wedges 710 and 720 at different heights substantially enable the divergence of the transmitted beam 705 to be characterized by determining the beam width BW at different heights, using the beam width equation described above.

Figure 10:
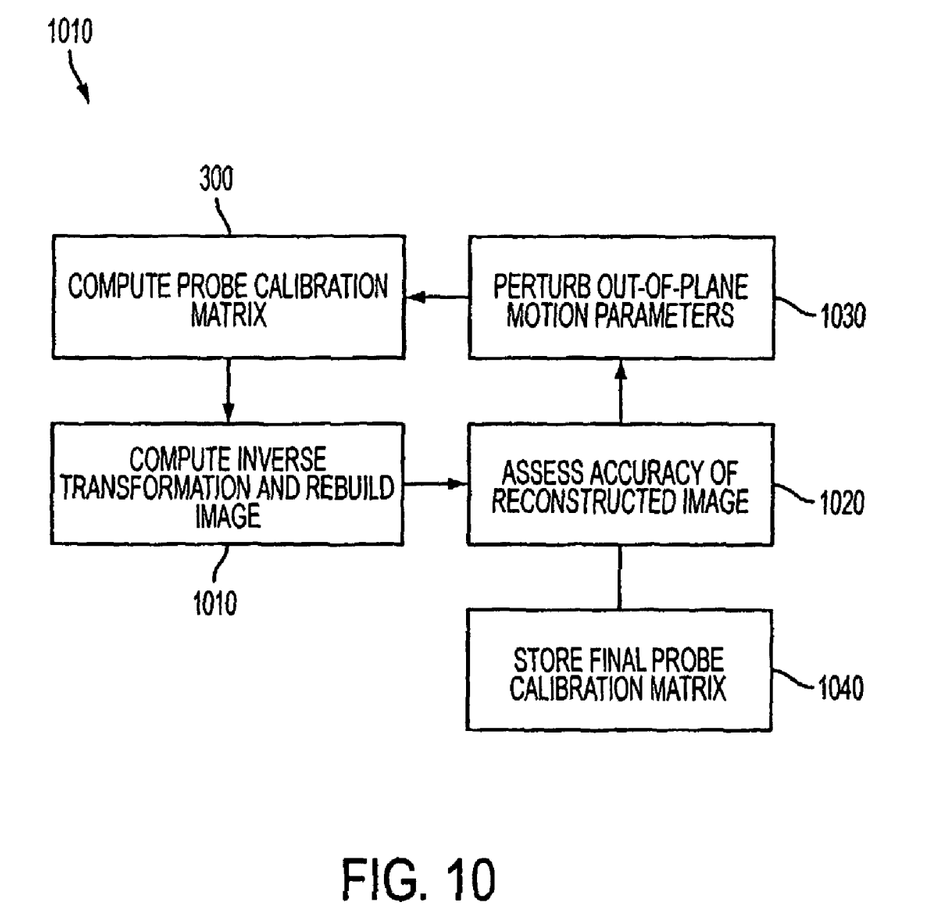
FIG. 10 illustrates an exemplary process for performing bootstrap calibration of an ultrasound probe according to the present invention.

Exemplary system 600 may be used in a "bootstrap calibration" procedure, in which the probe calibration matrix $^R T_P$ is iteratively refined, and its accuracy and precision are improved. FIG. 10 illustrates an exemplary process 1000 for performing bootstrap calibration according to the present invention.

Exemplary process 1000 includes process 300, in which ultrasound image data and probe position and angle data are collected. In this case, the ultrasound images include an image of one of the double-wedge phantoms 610 and the cross-wire structure 640. The bootstrapping calibration technique works more effectively if the cross-wire structure 640 within the field of view of the ultrasound probe 210, but as far from the double-wedge phantom 610 as practicable. Within process 300, the ultrasound probe 210 is placed such that it is sequentially centered and aligned relative to pose 1, pose 2, and pose 3. A probe calibration matrix $^R T_P$ is computed according to process 300. Process 300 is implemented in such a way that a plurality of images may be acquired at each pose, and the mean and standard deviation corresponding to the resulting probe calibration matrices are computed.

In step 1010, an inverse of the probe calibration matrix $^R T_P$ is computed, and the ultrasound image is reconstructed according to the inverse probe calibration matrix $^R T_P$. The reconstructed ultrasound image includes a reconstructed image of the cross-wire structure 640.

In step 1020, the reconstructed image of the cross-wire structure 640 is compared with an actual image of the cross-wire structure, and a standard deviation is computed between the two images. The accuracy of the reconstructed image of the cross-wire structure (and thus the accuracy of the probe calibration matrix $^R T_P$) is assessed according to pre-determined accuracy requirements. If the probe calibration matrix $^R T_P$ is deemed sufficiently accurate, the probe calibration matrix $^R T_P$ is stored; if not, process 1000 proceeds to step 1030.

In step 1030, the out-of-plane motion parameters are perturbed, and input into process 300 as a new estimate for the $U_k$, the transformation matrix from the coordinate frame of the double-wedge phantom 610 at pose k to the pixel coordinate frame 245. The purpose of perturbing the $U_k$ matrix is to substantially encompass the range of values for the elements of the $U_k$ matrix such that the optimal version of $U_k$ will be selected.

In an additional embodiment of the present invention, the system 200 illustrated in FIG. 2, in conjunction with exemplary process 300 illustrated in FIG. 3, may be implemented without the use of a phantom 260. In this exemplary embodiment, image registration may be done by use of speckle correlation. Speckle refers to a situation in which a target tissue contains a plurality of small acoustic scatterers that form patterns of constructive and destructive interference within the tissue. The speckle pattern is generally stable, and may provide a pattern with sufficient spatial variability to substantially enable computing correlations between successive ultrasound images.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method for spatially calibrating an ultrasound probe, comprising:
   placing the ultrasound probe in a first position and orientation relative to a phantom;
   measuring the first position and orientation of the ultrasound probe;

acquiring a first ultrasound image of the phantom;
determining a first spatial relationship between a phantom reference frame and a pixel reference frame, based on the first ultrasound image;
repositioning the ultrasound probe in a second position and orientation relative to the phantom;
measuring the second position and orientation of the ultrasound probe;
acquiring a second ultrasound image of the phantom;
determining a second spatial relationship between the phantom reference frame and the pixel reference frame, based on the second ultrasound image; and
computing a probe calibration matrix based on the first position and orientation of the ultrasound probe, the first spatial relationship, the second position and orientation of the ultrasound probe, and the second spatial relationship.

2. The method of claim 1, further comprising acquiring position and orientation data from position and angle encoder.

3. The method of claim 1, wherein determining the first spatial relationship includes:
identifying prominent phantom feature points in the first ultrasound image;
identifying a center point of the phantom; and
determining a coordinate transformation between the center point of the phantom and a reference frame corresponding to the ultrasound probe.

4. The method of claim 3, wherein determining a coordinate transformation between the center point of the phantom and a reference frame corresponding to the ultrasound probe includes:
determining a translation between the center point of the phantom and a pixel location in the reference frame of the ultrasound probe; and
determining a rotation between the center point of the phantom and a pixel location in the reference frame of the ultrasound probe.

5. The method of claim 4, wherein determining a rotation between the center point of the phantom and a pixel location in the reference frame of the ultrasound probe includes representing the rotation as a quaternion.

6. The method of claim 1, wherein determining a first spatial relationship includes representing the first spatial relationship as a quaternion.

7. The method of claim 6, wherein extracting a unique solution includes using a unity constraint to a first nine coefficients representing a rotation component to the calibration matrix.

8. The method of claim 1, wherein determining a first spatial relationship includes representing the first spatial relationship as a transformation matrix.

9. The method of claim 1, wherein computing a probe calibration matrix includes:
assembling the first position and orientation of the ultrasound probe, the first spatial relationship, the second position and orientation of the ultrasound probe, and the second spatial relationship into a closed form formulation; and
extracting a unique solution from a null space corresponding to the closed form formulation.

10. The method of claim 1, wherein computing a probe calibration matrix includes:
assembling the first position and orientation of the ultrasound probe, the first spatial relationship, the second position and orientation of the ultrasound probe, and the second spatial relationship into a closed form formulation;
extracting a rotational component from a null space corresponding to the closed form formulation;
extracting a translational component from the null space corresponding to the closed form formulation; and
extracting a vector of scale factors from the null space corresponding to the closed form formulation.

11. The method of claim 1, wherein measuring the first position and orientation of the ultrasound probe includes using optical markers that are disposed on the ultrasound probe.

12. The method of claim 1, wherein placing the ultrasound probe in a first position relative to a phantom includes placing the ultrasound probe in contact with a docking station, the docking station having a position and orientation that is substantially fixed relative to the phantom.

13. A system for performing intra-operative calibration of an ultrasound probe, comprising:
a position and angle encoder for measuring a position and angle of the ultrasound probe;
a phantom providing a reference element and
a data system configured [having a computer readable medium encoded with a program] for computing a probe calibration matrix according to a closed form formulation, and according to a relative change between a first location corresponding with the reference element in a first ultrasound image and a second location corresponding with the reference element in a second ultrasound image, wherein the first ultrasound image corresponds to a first ultrasound probe position, and the second ultrasound image corresponds to a second ultrasound probe position.

14. The system of claim 13, wherein the first location includes a prominent feature point.

15. The system of claim 13, wherein the first location includes a speckle pattern.

16. The system of claim 13, wherein the phantom includes a wire arranged substantially in an N-shape.

17. The system of claim 13, wherein the phantom includes two substantially parallel plates.

18. The system of claim 13, wherein the phantom includes two wedges.

19. The system of claim 13, further comprising a docking station, the docking station having a substantially fixed position and orientation.

20. The system of claim 13, wherein the position and angle encoder includes optical markers that are disposed on the ultrasound probe.

* * * * *